(12) United States Patent
Tanghal

(10) Patent No.: US 11,571,273 B2
(45) Date of Patent: Feb. 7, 2023

(54) MARKER DELIVERY DEVICE AND METHOD OF DEPLOYING A MARKER

(71) Applicant: Devicor Medical Products, Inc., Cincinnati, OH (US)

(72) Inventor: Emmanuel Tanghal, Mason, OH (US)

(73) Assignee: Devicor Medical Products, Inc., Cincinnti, OH (US)

( * ) Notice: Subject to any disclaimer, the term of this patent is extended or adjusted under 35 U.S.C. 154(b) by 1215 days.

(21) Appl. No.: 15/975,892

(22) Filed: May 10, 2018

(65) Prior Publication Data

US 2018/0318036 A1  Nov. 8, 2018

Related U.S. Application Data

(63) Continuation of application No. PCT/US2016/061170, filed on Nov. 9, 2016.

(60) Provisional application No. 62/254,018, filed on Nov. 11, 2015.

(51) Int. Cl.
*A61B 90/00* (2016.01)
*A61B 5/06* (2006.01)

(52) U.S. Cl.
CPC .............. *A61B 90/39* (2016.02); *A61B 5/064* (2013.01); *A61B 2090/3908* (2016.02); *A61B 2090/3912* (2016.02); *A61B 2090/3987* (2016.02)

(58) Field of Classification Search
CPC .............................................. A61B 2090/3987
See application file for complete search history.

(56) References Cited

U.S. PATENT DOCUMENTS

| | | |
|---|---|---|
| 421,072 A | 2/1890 | Harris |
| 2,828,744 A | 4/1958 | Hirsch et al. |
| 4,787,384 A | 11/1988 | Campbell et al. |
| 5,002,548 A | 3/1991 | Campbell et al. |
| 5,024,727 A | 6/1991 | Campbell et al. |
| 5,526,822 A | 6/1996 | Burbank et al. |
| 5,853,366 A | 12/1998 | Dowlatshahi |
| 5,906,574 A | 5/1999 | Kan |
| 5,928,164 A | 7/1999 | Burbank et al. |
| 5,941,890 A | 8/1999 | Voegele et al. |
| 6,017,316 A | 1/2000 | Ritchart et al. |
| 6,086,544 A | 7/2000 | Hibner et al. |

(Continued)

FOREIGN PATENT DOCUMENTS

| | | |
|---|---|---|
| WO | WO 1997/017103 A1 | 5/1997 |
| WO | WO 2001/008578 | 2/2001 |

(Continued)

OTHER PUBLICATIONS

European Communication dated Mar. 24, 2020 for Application No. 16798353.5, 6 pages.

(Continued)

*Primary Examiner* — Rochelle D Turchen
(74) *Attorney, Agent, or Firm* — Frost Brown Todd LLP

(57) ABSTRACT

A marker delivery device is described and claims. The marker delivery device is used to implant a detectable marker after a biopsy procedure is performed. The marker delivery device includes a cannula comprising a distal end and a marker exit positioned proximate the distal end; a rod extending within the cannula; and a flexible deployer operatively coupled with the rod and positioned proximate the marker exit.

17 Claims, 4 Drawing Sheets

(56) References Cited

U.S. PATENT DOCUMENTS

| | | |
|---|---|---|
| 6,161,034 A | 12/2000 | Burbank et al. |
| 6,162,187 A | 12/2000 | Buzzard et al. |
| 6,162,241 A | 12/2000 | Coury et al. |
| 6,220,248 B1 | 4/2001 | Voegele et al. |
| 6,228,055 B1 | 5/2001 | Foerster et al. |
| 6,231,494 B1 | 5/2001 | Verin et al. |
| 6,245,090 B1 | 6/2001 | Gilson et al. |
| 6,270,464 B1 | 8/2001 | Fulton, III et al. |
| 6,270,472 B1 | 8/2001 | Antaki et al. |
| 6,347,241 B2 | 2/2002 | Burbank et al. |
| 6,356,782 B1 | 3/2002 | Sirimanne et al. |
| 6,371,904 B1 | 4/2002 | Sirimanne et al. |
| 6,427,081 B1 | 7/2002 | Burbank et al. |
| 6,432,065 B1 | 8/2002 | Burdorff et al. |
| 6,450,938 B1 | 9/2002 | Miller |
| 6,544,185 B2 | 4/2003 | Montegrande |
| 6,567,689 B2 | 5/2003 | Burbank et al. |
| 6,626,849 B2 | 9/2003 | Huitema et al. |
| 6,654,629 B2 | 11/2003 | Montegrande |
| 6,662,041 B2 | 12/2003 | Burbank et al. |
| 6,689,056 B1 | 2/2004 | Kilcoyne et al. |
| 6,699,205 B2 | 3/2004 | Fulton, III et al. |
| 6,725,083 B1 | 4/2004 | Burbank et al. |
| 6,730,042 B2 | 5/2004 | Fulton et al. |
| 6,752,768 B2 | 6/2004 | Burdorff et al. |
| 6,790,185 B1 | 9/2004 | Fisher et al. |
| 6,824,507 B2 | 11/2004 | Miller |
| 6,862,470 B2 | 3/2005 | Burbank et al. |
| 6,889,833 B2 | 5/2005 | Seiler et al. |
| 6,993,375 B2 | 1/2006 | Burbank et al. |
| 6,996,433 B2 | 2/2006 | Burbank et al. |
| 7,044,957 B2 | 5/2006 | Foerster et al. |
| 7,047,063 B2 | 5/2006 | Burbank et al. |
| 7,063,681 B1 | 6/2006 | Peery |
| 7,104,945 B2 | 9/2006 | Miller |
| 7,229,417 B2 | 6/2007 | Foerster et al. |
| 7,247,160 B2 | 7/2007 | Seiler et al. |
| 7,329,414 B2 | 2/2008 | Fisher et al. |
| 7,407,054 B2 | 8/2008 | Seiler et al. |
| 7,429,240 B2 | 9/2008 | Miller |
| 7,442,171 B2 | 10/2008 | Stephens et al. |
| 7,465,279 B2 | 12/2008 | Beckman et al. |
| 7,575,556 B2 | 8/2009 | Speeg et al. |
| 7,648,466 B2 | 1/2010 | Stephens et al. |
| 7,668,582 B2 | 2/2010 | Sirimanne et al. |
| 7,837,632 B2 | 11/2010 | Stephens et al. |
| 7,854,706 B2 | 12/2010 | Hibner |
| 7,914,464 B2 | 3/2011 | Burdorff et al. |
| 7,938,786 B2 | 5/2011 | Ritchie et al. |
| 8,068,895 B2 | 11/2011 | Speeg et al. |
| 8,079,964 B2 | 12/2011 | Reichel et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,241,299 B2 | 8/2012 | Hibner |
| 8,251,916 B2 | 8/2012 | Speeg et al. |
| 8,320,993 B2 | 11/2012 | Sirimanne et al. |
| 8,371,443 B2 | 2/2013 | Nock et al. |
| 8,414,602 B2 | 4/2013 | Selis |
| 8,454,531 B2 | 6/2013 | Speeg et al. |
| 8,532,747 B2 | 9/2013 | Nock et al. |
| 8,600,481 B2 | 12/2013 | Sirimanne et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 2003/0109803 A1 | 6/2003 | Huitema et al. |
| 2004/0030262 A1 | 2/2004 | Fisher et al. |
| 2004/0204660 A1 | 10/2004 | Fulton et al. |
| 2004/0236213 A1 | 11/2004 | Jones et al. |
| 2005/0033195 A1 | 2/2005 | Fulton et al. |
| 2005/0080338 A1 | 4/2005 | Sirimanne et al. |
| 2005/0085724 A1 | 4/2005 | Sirimanne et al. |
| 2005/0119562 A1 | 6/2005 | Jones et al. |
| 2005/0228311 A1 | 10/2005 | Beckman et al. |
| 2006/0036159 A1 | 2/2006 | Sirimanne et al. |
| 2006/0036165 A1 | 2/2006 | Burbank et al. |
| 2006/0074345 A1 | 4/2006 | Hibner |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0084865 A1 | 4/2006 | Burbank et al. |
| 2006/0122503 A1 | 6/2006 | Burbank et al. |
| 2006/0155190 A1 | 7/2006 | Burbank et al. |
| 2006/0224082 A1 | 10/2006 | Vetter et al. |
| 2006/0276680 A1 | 12/2006 | Seiler et al. |
| 2007/0010738 A1 | 1/2007 | Mark et al. |
| 2007/0016017 A1 | 1/2007 | Mark et al. |
| 2007/0021714 A1 | 1/2007 | Miller |
| 2007/0118048 A1 | 5/2007 | Stephens et al. |
| 2007/0135711 A1 | 6/2007 | Chernomorsky et al. |
| 2007/0142725 A1 | 6/2007 | Hardin et al. |
| 2007/0254005 A1 | 11/2007 | Pathak et al. |
| 2008/0033280 A1 | 2/2008 | Lubock et al. |
| 2008/0039819 A1 | 2/2008 | Jones et al. |
| 2008/0058640 A1 | 3/2008 | Jones et al. |
| 2008/0195066 A1 | 8/2008 | Speeg et al. |
| 2009/0131821 A1 | 5/2009 | Speeg et al. |
| 2009/0192408 A1 | 7/2009 | Mark |
| 2009/0216150 A1 | 8/2009 | Reichel et al. |
| 2009/0281453 A1* | 11/2009 | Tsonton ............... A61B 90/17 600/567 |
| 2010/0152610 A1 | 6/2010 | Parihar et al. |
| 2010/0160819 A1 | 6/2010 | Parihar et al. |
| 2010/0286627 A1* | 11/2010 | Hardin ............... A61B 90/39 604/264 |
| 2013/0237912 A1 | 9/2013 | Speeg |
| 2013/0324882 A1 | 12/2013 | Mescher |
| 2014/0276037 A1 | 9/2014 | Johnson et al. |
| 2015/0360019 A1* | 12/2015 | Clancy ............. A61M 37/0069 600/432 |
| 2016/0128784 A1* | 5/2016 | Ahari ................... A61B 10/02 600/432 |
| 2018/0140288 A1* | 5/2018 | Householder ...... A61B 10/0275 |

FOREIGN PATENT DOCUMENTS

| | | |
|---|---|---|
| WO | WO 2003/051452 A1 | 6/2003 |
| WO | WO 2007/069105 A2 | 6/2007 |

OTHER PUBLICATIONS

International Search Report and Written Opinion for International Application No. PCT/US2016/061170, dated Dec. 21, 2016, 9 pages.

Partial European Search Report for Application Serial No. 09250485, dated Jun. 17, 2009.

U.S. Appl. No. 60/869,736, entitled "Biopsy System," filed Dec. 13, 2006.

U.S. Appl. No. 60/874,792, entitled "Biopsy Sample Storage," filed Dec. 13, 2006.

* cited by examiner

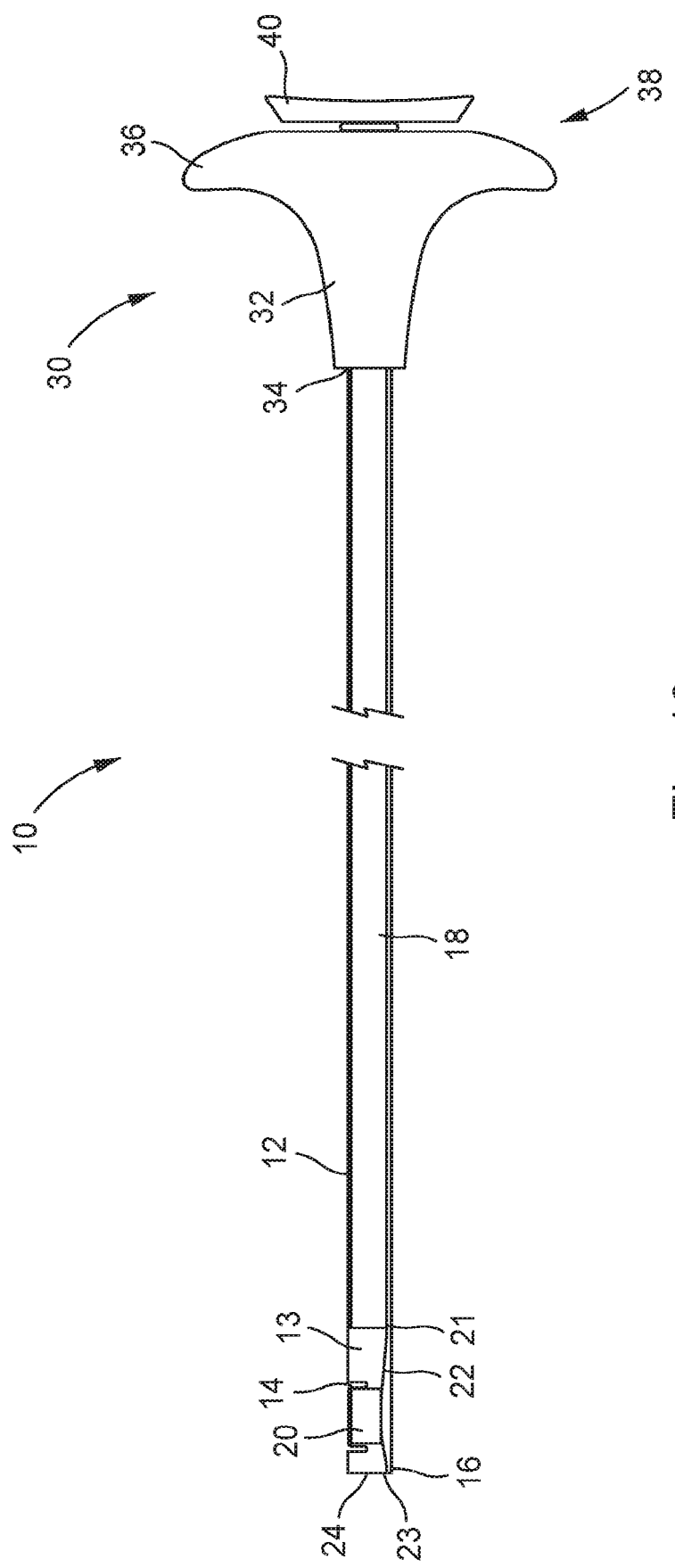

MARKER DELIVERY DEVICE AND METHOD OF DEPLOYING A MARKER

RELATED APPLICATION

The present Application for patent claims priority to U.S. Provisional Application No. 62/254,018 entitled "MARKER DELIVERY DEVICE AND METHOD OF DEPLOYING A MARKER" filed Nov. 11, 2015, which is assigned to the assignee hereof, and incorporated herein by reference in its entirety.

FIELD OF THE INVENTION

The present invention relates generally to marker delivery devices and methods of deploying a marker.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise.

Example biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 30, 2003; U.S. Pat. No. 7,442,171, entitled "Remote Thumbwheel for a Surgical Biopsy Device," issued Oct. 28, 2008; U.S. Pat. No. 7,938,786, entitled "Vacuum Timing Algorithm for Biopsy Device," issued May 10, 2011; U.S. Pat. No. 8,118,755, entitled "Biopsy Sample Storage," issued Feb. 21, 2012; U.S. Pat. No. 9,095,326, entitled "Biopsy System with Vacuum Control Module," issued Aug. 4, 2015; U.S. Pat. No. 8,251,916, entitled "Revolving Tissue Sample Holder for Biopsy Device," issued Aug. 28, 2012; and U.S. Pat. No. 8,532,747, entitled "Biopsy Marker Delivery Device," issued Sep. 10, 2013. The disclosure of each of the above-cited U.S. patents and U.S. patent application Publications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, CORMARK™, HYDROMARK®, and MAMMOSTAR™ brand devices from Devicor Medical Products, Inc. of Cincinnati, Ohio. Further example devices and methods for marking a biopsy site are disclosed in U.S. Pat. Nos. 7,465,279; 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002, U.S. Pub. No. 2014/0276037, entitled "Biopsy Site Marker Applier," published Sep. 18, 2004; U.S. Pub. No. 2013/0237912, entitled "Biopsy Marker Delivery Device," published Sep. 12, 2013; U.S. Pat. No. 8,371,443, entitled "Biopsy Marker Delivery Device," issued Sep. 10, 2013; U.S. Pat. No. 8,241,299, entitled "Biopsy Marker Delivery Configured to Retain Marker Prior to Intended Deployment," issued Aug. 14, 2012; U.S. Pat. No. 8,068,895, entitled "Biopsy Site Marker Deployment Instrument," issued Nov. 14, 2011; and U.S. Pat. No. 8,414,602, entitled "Biopsy Device and Methods," issued Apr. 9, 2013. The disclosure of each of the above-cited U.S. patents and U.S. patent application Publications is incorporated by reference herein.

However, when operating some of the above-described marker deployment devices, there is a risk that the marker will not fully deploy. When the marker is not fully deployed the marker may become snagged in the biopsy device and shift from its intended position. In some devices, there is also the risk of the tip of the deployment rod over-extending through the aperture of the biopsy device. Over-extension may lead to a risk of the over-extended portion being shorn off by the biopsy device's aperture and left inside the patient. Thus, there is a need in the art for a marker deployment system that minimizes or prevents these problems.

SUMMARY OF THE INVENTION

Aspects of the present invention provide, among other variations, a marker delivery device including a cannula comprising a distal end and a marker exit positioned proximate the distal end, a rod extending within the cannula, and a flexible deployer operatively coupled with the rod and positioned proximate the marker exit.

Another aspect of the present invention provides a method of deploying a marker including translating a rod within a cannula, the cannula comprising a distal end and a marker exit positioned proximate the distal end, flexing a flexible deployer operatively coupled with the rod and positioned proximate the marker exit, wherein the translating of the rod flexes the flexible deployer, and expelling the marker out of the marker exit, wherein the flexing of the flexible deployer expels the marker Additional advantages and novel features of various aspects of the present invention will be set forth in part in the description that follows, and in part will become more apparent to those skilled in the art upon examination of the following or upon learning by practice thereof.

BRIEF DESCRIPTION OF THE FIGURES

In the drawings:

FIG. 10 is a side view of the example marker delivery device of FIG. 1 showing an example operative end.

DETAILED DESCRIPTION

Figure 1:
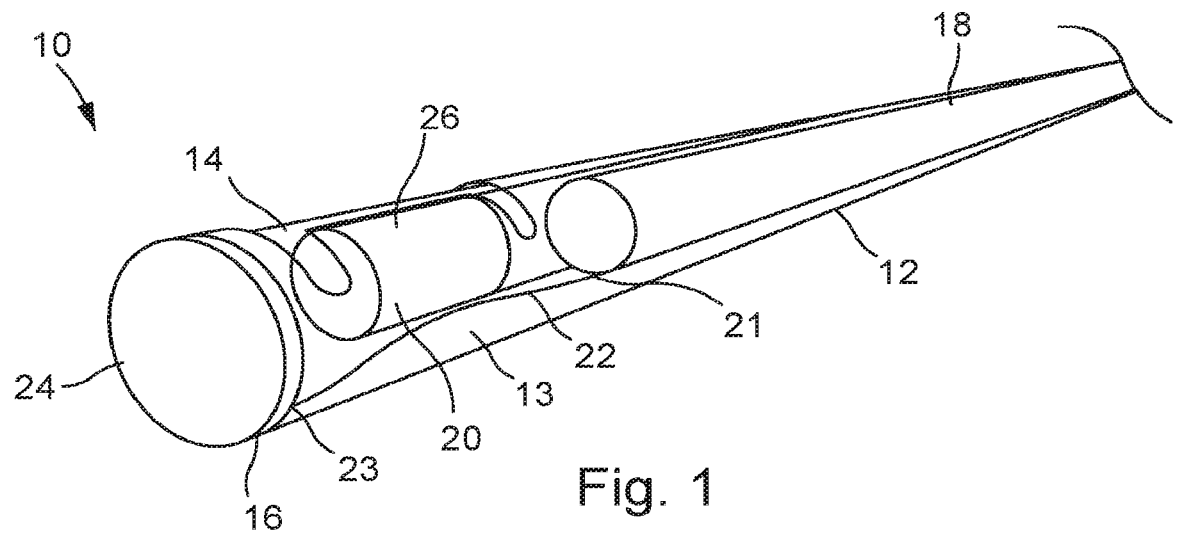
FIG. 1 is a perspective view of an example marker delivery device in a pre-actuated state in accordance with aspects of the present invention.

The following description of certain examples of the invention should not be used to limit the scope of the present invention. Other examples, features, aspects, embodiments, advantages, and one of the best modes contemplated for carrying out of the invention will become apparent to those skilled in the art from the following description, which is by way of illustration only, and in no way designed to limit the scope of the present invention. As will be realized, the present invention is capable of other different and obvious aspects, all without departing from the scope of the present invention. Accordingly, the drawings and descriptions should be regarded as illustrative in nature and not restrictive.

An aspect of the present invention provides, among other features, a marker delivery device comprising a cannula including a distal end and a marker exit positioned proximate the distal end, a rod extending within the cannula, and a flexible deployer operatively coupled with the rod and positioned proximate the marker exit.

Another aspect of the present invention provides, among other features, a method of deploying a marker, comprising translating a rod within a cannula, the cannula comprising a distal end and a marker exit positioned proximate the distal end, flexing a flexible deployer operatively coupled with the rod and positioned proximate the marker exit, wherein the translating of the rod flexes the flexible deployer, and expelling the marker out of the marker exit, wherein the flexing of the flexible deployer expels the marker.

Parts List

| Part Names | Number |
| --- | --- |
| device | 10 |
| cannula | 12 |
| lumen | 13 |
| exit | 14 |
| distal end | 16 |
| rod | 18 |
| marker | 20 |
| first end (2) | 21 |
| flexible deployer | 22 |
| second end | 23 |
| end cap | 24 |
| flexible flaps | 26 |
| operative end | 30 |
| hub | 32 |
| proximal end | 34 |
| grip | 36 |
| actuator | 38 |
| plunger | 40 |

FIGS. 1-8 provide examples illustrating the deployment end (e.g., the end where the marker is deployed) of a marker delivery device 10 which includes an elongate outer cannula 12 defining a lumen 13 therein. The cannula 12 may include a marker exit 14, such as side opening formed adjacent to, but spaced proximally from, the distal end 16 of the cannula 12. A rod 18 may extend within lumen 13 of the cannula 12 for acting upon a marker 20 during operation.

Operative end 30, not shown in FIGS. 1-9, is where the user operates the device. An example operative end 30 is shown in FIG. 10 and is described separately below. The operative end 30 may include a hub coupled with a proximal end of the cannula 12 and include a grip. An actuator may be provided that translates the rod 18 within the lumen 13 of the cannula 12 when the actuator is actuated. For example, the actuator may include a plunger coupled with the rod 18. The rod 18 may have sufficient rigidity in compression to push the marker 20 from an internal lumen of the cannula 12 out through the exit 14. The rod 18 may also be relatively flexible. The plunger may be coupled at the proximal end of the rod 18 for forcing the rod 18 distally in the lumen 13 of the cannula 12 to deploy the marker 20 out of the cannula 12. In operation, the user may grasp the grip with two fingers of one hand, and may push on plunger using the thumb on the same hand, so that marker delivery device 10 is operated by a user's single hand. A spring or other feature may be provided about rod 18 to bias rod 18 proximally relative to the grip and the cannula 12.

The cannula 12 may be formed of any suitable metallic or non-metallic material. In some versions, the cannula 12 is formed of a thin walled hollow tube formed of a suitable medical grade plastic or polymer. One suitable material is a thermoplastic elastomer, such as Polyether block amide (PEBA), available commercially for sale under the tradename PEBAX, see http://www.pebax.com/en/pebax-range/product-viewer/Pebaxsup-sup-00001/. The cannula 12 may be formed of PEBAX, and may be substantially transparent to visible light and X-ray. The rod 18 may be formed of the same or different material.

The operative end of the device 10 may include any suitable structure for allowing the operator to grip the device and actuate the rod 18. That is, the deployment features described herein are applicable to any type of marker deployment device in which a rod is used to expel the marker. For example, the actuator, the grip, and/or the plunger may be as disclosed in any of the above-noted references, e.g., U.S. Pat. Nos. 6,371,904; 6,993,375; 6,996,433; 7,044,957; 7,047,063; 7,229,417; 7,465,279; 8,068,895; 8,241,299; 8,371,443 and 8,414,602, and U.S. Published Patent Application Number 2013/0237912, now abandoned and U.S. Published Patent Application Number 2014/0276037; which patents and patent applications are all incorporated by reference.

Figure 3:
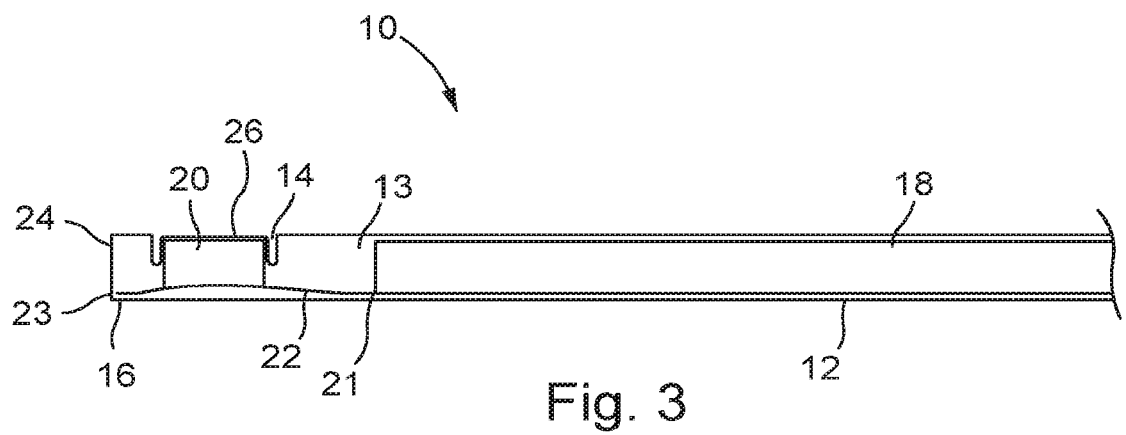
FIG. 3 is a side view of the example marker delivery device of FIG. 1 in the pre-actuated state.
Figure 4:
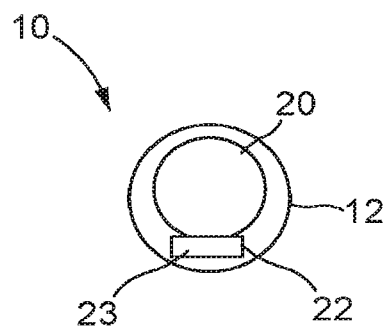
FIG. 4 is a front view of the example marker delivery device of FIG. 2 in the pre-actuated state.
Figure 5:
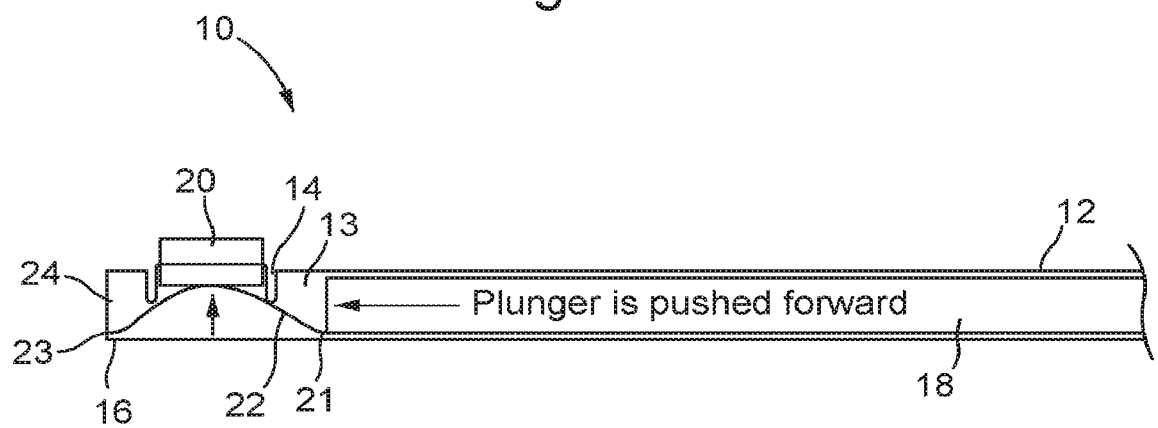
FIG. 5 is a side view of the example marker delivery device of FIG. 1 in a partially-actuated state.
Figure 6:
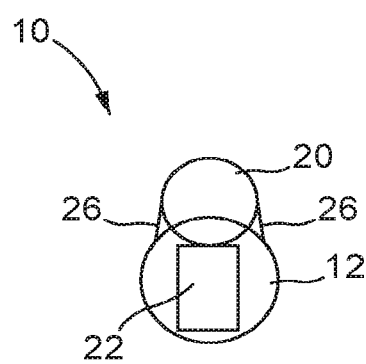
FIG. 6 is a front view of the example marker delivery device of FIG. 1 in the partially-actuated state.
Figure 7:
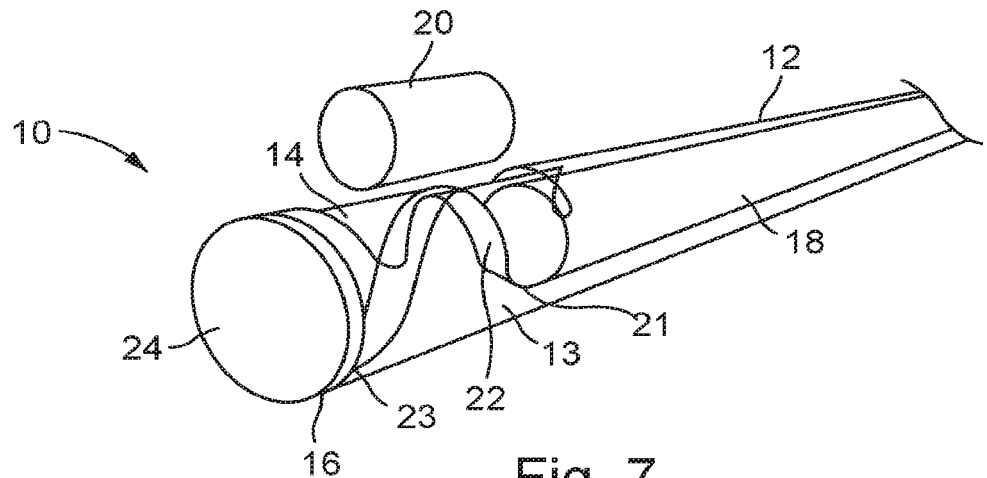
FIG. 7 is a perspective view of the example marker delivery device of FIG. 1 in a post-actuated state.
Figure 8:
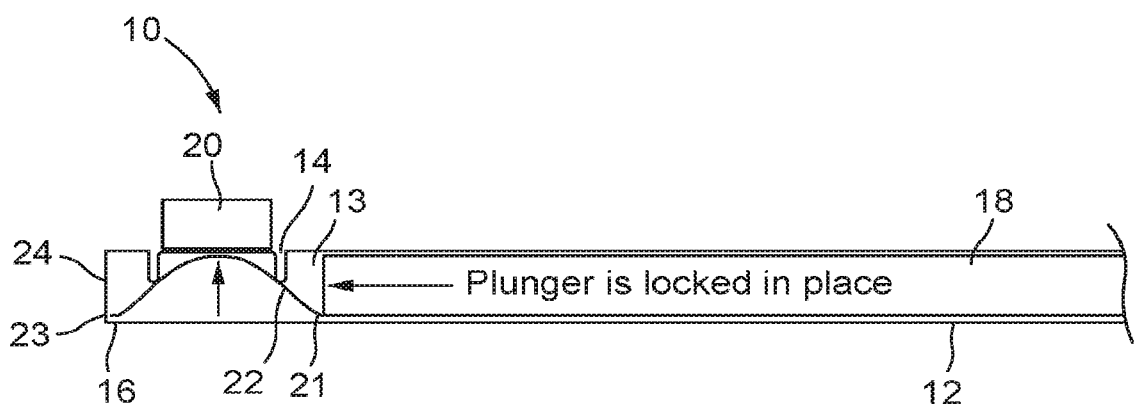
FIG. 8 is a side view of the example marker delivery device of FIG. 1 in the post-actuated state.
Figure 9:
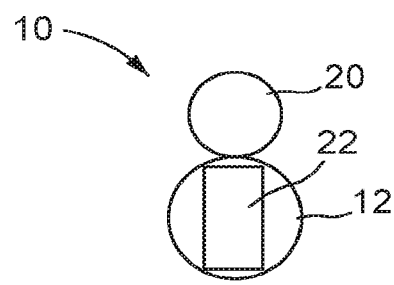
FIG. 9 is a front view of the example marker delivery device of FIG. 1 in the post-actuated state.

FIGS. 1-4 show the deployment end of the example marker deployment device 10 in a pre-actuated state. FIGS. 5 and 6 show the deployment end of the marker deployment device 10 in a partially actuated state. FIGS. 7-9 show the deployment end of the marker deployment device 10 in a fully actuated state. In the front views of FIGS. 4, 6, and 9, the end of the device is transparent so that the inside elements can be viewed.

Figure 2:
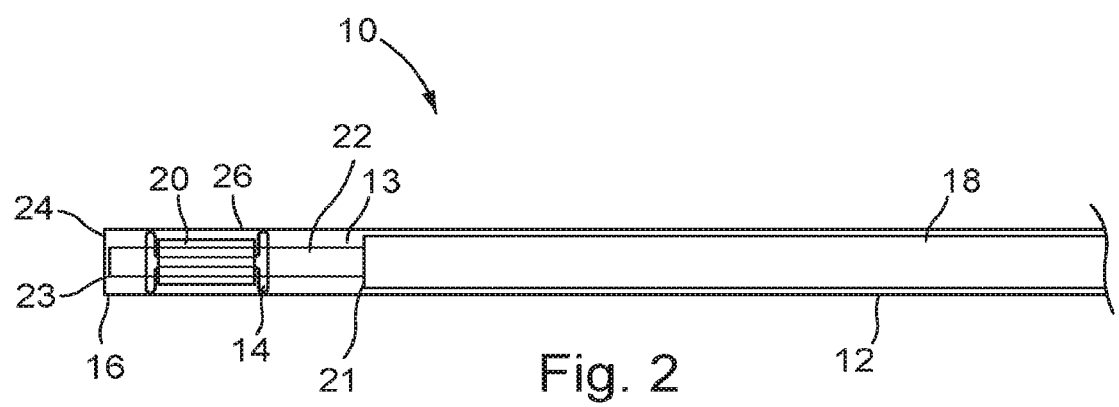
FIG. 2 is a top view of the example marker delivery device of FIG. 1 in the pre-actuated state.

As best seen in FIGS. 1, 3, 5, 7, and 8, the marker deployment device 10 may further include a flexible deployer 22. The flexible deployer 22 may be integral with or separately attached to the rod 18 at a first end 21 of the rod 18. The flexible deployer 22 may be made from the same or different material as the rod 18. As seen in FIGS. 1 and 3, in the pre-actuated state, the flexible deployer may be relatively flat, e.g., extending substantially parallel to an inner surface of the cannula 12 or parallel to the longitudinal axis of the cannula. That is, in the pre-actuated state, the flexible deployer 22 is in a non-flexed state. As best seen in FIGS. 1-3, in the pre-actuated state, the flexible deployer 22 may extend from the rod 18 such that a second end 23 of the flexible deployer 22 terminates at, or substantially at, an end cap 24 of the cannula 12. Furthermore, as seen in FIGS. 1, 3, and 4, in the pre-actuated state, the marker 20 is completely contained within cannula 12 and rests on top of flexible deployer 22. The flexible deployer 22 may have sufficient resiliency such that the flexible deployer 22 is biased to the position shown in FIGS. 1-4 prior to force being applied by the operator.

The exit 14 of the cannula 12 may be defined and partially or fully enclosed by pair of flexible flaps 26. As best seen in FIGS. 1 and 2, the flexible flaps 26 may cover the marker 20 in the pre-actuated state. The flexible flaps 26 may have sufficient resiliency such that the flexible flaps 26 are biased to the position shown in FIGS. 1 and 2 prior to force being applied by the operator. That is, the flexible flaps 26 may act as a door that blocks the marker 20 from exiting the cannula 12, absent the intentional application of force on the rod 18. In this manner, the marker 20 may rest just underneath the exit 14, without the risk of the marker 20 unintentionally being released from the cannula 12.

When it is desirable to release the marker 20 from the cannula 12, the operator may begin to apply force on the rod 18 to translate the rod 18 toward the end cap 24 at the distal end of the cannula 12. As noted above, the movement of the rod 18 may be achieved by any known actuation mechanism, and in particular, any actuation mechanism disclosed in the U.S. patents and U.S. Published patent applications incorporated by reference above. As the rod 18 begins to translate toward the end cap 24, the flexible deployer 22 begins to flex upwardly, e.g., perpendicularly relative to the longitudinal axis of cannula 12. The flexing of the flexible deployer 22 occurs because the rod 18 is integral with or attached to the flexible deployer 22 at the first end 21. Moving the rod 18 forces the second end 23 of the flexible deployer 22 to push against the end cap 24. As the rod 18 continues to be pushed toward the end cap 24, the flexible deployer 22 continues to flex toward the flexible flaps 26. Because the marker 20 rests on the flexible deployer 22, the flexing of the flexible deployer 22 also causes the marker 20 to move upwardly toward the flexible flaps 26 (e.g., substantially perpendicular to the longitudinal axis of the cannula) and press against the flexible flaps 26. As more force is applied on the rod 18, more force is in turn applied to the flexible deployer 22, and more force is in turn is applied against the flexible flaps 26 by the marker 20. The application of force continues until the flexible flaps 26 are forced opened and marker begins pushing through the exit 14, exit 14 becoming enlarged with the flexible flaps 26 being opened.

As shown in FIGS. 5 and 6, during a point of partial actuation, where the rod 18 has been pushed some of the way, but not completely, the marker 20 partly extends out of the exit 14 and the flexible flaps 26 contact the sides of the marker 20.

After the partial actuation state, with the application of further force on the rod 18, the fully actuated state shown in FIGS. 7-9 will be reached. As shown in FIGS. 7-9, the rod 18 has been translated fully within the cannula 12 and the flexible deployer 22 has been fully flexed sufficient to completely eject the marker 20 out of the cannula 12. With the marker 20 having exited beyond the flexible flaps 26, the resiliency of the flaps biases the flaps back downward to their original position prior to the start of actuation. That is, because the marker 20 is no longer applying opening pressure on the flexible flaps 26 (via the flexible deployer 22), the flexible flaps 26 will close. Because the flexible flaps 26 are now closed, the marker 20 is prevented from inadvertently returning into the cannula 12.

The marker deployment device described herein may be used in conjunction with any suitable biopsy device known in the art used as part of a biopsy procedure. For example, the marker deployment device may used in conjunction with any of the biopsy devices described in U.S. Pat. Nos. 5,526,822; 6,086,544; 6,626,849; 7,442,171; 7,938,786; 8,118,755; 8,251,916; 8,532,747 and 9,095,326.

FIG. 10 shows the marker deployment device 10 with an example operative end 30. The operative end 30 may include a hub 32 coupled with a proximal end 34 of the cannula 12 and include a grip 36. An actuator 38 may be provided that translates the rod 18 within the lumen 13 of the cannula 12 when the actuator 38 is actuated. For example, the actuator 38 may include a plunger 40 coupled with the rod 18. In operation, the user may grasp the grip 36 with two fingers of one hand, and may push on plunger 40 using the thumb on the same hand, so that marker delivery device 10 is operated by a user's single hand.

The marker may be any suitable marker known in the art. See the markers described and claimed in U.S. Pat. Nos. 5,941,890, 6,162,241, 6,270,464, 6,356,782, 6,790,185, 7,668,582 8,068,895, 8,320,993 and 8,600,481.

For example, as described in U.S. Pat. No. 8,068,895 the marker may comprise a marker body and a marking element. In some variations, the marker body may be visible under ultrasound imaging, while the marking element may be visible under MRI and X-ray, among other imaging modalities. For instance, the marker body may be formed of polyethylene glycol hydrogel, bovine collagen, cellulose, beta glucan, Polylactic acid/Polyglycolide, Glycoprene® implantable grade polymers available from http://poly-med.com/services/implantable-grade-polymers-catalogue/glycoprene/, gelatinous materials such as hydrogel, and/or any other suitable material(s), including combinations thereof. Furthermore, the marker body may be biodegradable or bioabsorbable, or may have other properties. The marking element may comprise a stainless steel structure, a titanium structure, a ceramic structure, a pellet, or other suitable geometric shaped structure. Any other material(s) may be used for the marking element, including combinations thereof. In some variations, the marker body may be formed of a square collagen pad that is folded and/or rolled about a titanium the marking element to form a substantially cylindraceous marker. The marker may then be compressed radially inward in this example before being inserted into the cannula for deployment. The marker may have a variety of alternative configurations, may be formed using a variety of techniques, and may be used in a variety of other ways as described in some of the U.S. patents and U.S. patent application Publications incorporated by reference above.

While this invention has been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

The invention claimed is:

1. A marker delivery device, comprising:
   a cannula including a closed distal end and a side aperture positioned proximate the closed distal end;
   a pair of flexible flaps extending from the cannula to cover at least a portion of the side aperture, the pair of flexible flaps being biased to cover a marker disposed within the cannula;
   a rod extending within the cannula; and a flexible deployer operatively coupled with the rod and positioned proximate the side aperture, the flexible deployer being configured to transition from a pre-actuated state to an actuated state, the rod being configured to transition the flexible deployer to the actuated state to thereby expel a biopsy site marker through the pair of flexible flaps and out of the side aperture.

2. The marker delivery device of claim 1, the flexible deployer being a strip configured to buckle in response to translation of the rod to thereby expel the biopsy site marker from the side aperture.

3. The marker delivery device of claim 2, the flexible deployer being configured to rest proximate an inner surface of the cannula when the flexible deployer is in the pre-actuated state.

4. The marker delivery device of claim 1, the flexible deployer being positioned opposite of the side aperture, the flexible deployer being configured to permit the biopsy site marker to be completely contained within the cannula when the flexible deployer is in the pre-actuated state.

5. The marker delivery device of claim 2, the flexible deployer being resiliently biased to the pre-actuated state.

6. The marker delivery device of claim 2, the flexible deployer being configured to transition from the pre-actuated state to the actuated state upon distal translation of the rod within the cannula.

7. The marker delivery device of claim 1, the flexible deployer extending distally from the rod and terminating proximate to the closed distal end of the cannula.

8. The marker delivery device of claim 1, the flexible deployer being integral with the rod.

9. The marker delivery device of claim 1, the flexible deployer being separately attached to the rod.

10. A marker delivery device, comprising:
(a) a cannula including a closed distal end and a side aperture positioned proximally relative to the closed distal end, the cannula defining a pair of flexible flaps associated with the side aperture;
(b) a rod movable within the cannula relative to the side aperture; and
(d) a flexible deployer resiliently biased towards a non-flexed configuration extending parallel to a longitudinal axis defined by the cannula and configured to deform from the non-flexed configuration in response to movement of the rod to expel a biopsy site marker through the pair of flexible flaps and out of the side aperture.

11. The marker delivery device of claim 10, the flexible deployer being secured to the rod and extending from the rod to the closed distal end of the cannula, the flexible deployer being configured to deform orthogonally relative to the longitudinal axis of the cannula in response to distal translation of the rod.

12. The marker delivery device of claim 10, the rod being configured to translate within the cannula to buckle the flexible deployer orthogonally relative to the longitudinal axis of the cannula and thereby expel the biopsy site marker from the side aperture.

13. The marker delivery device of claim 10, the pair of flexible flaps being configured to block movement of the biopsy site marker through the side aperture when the flexible deployer is in the non-flexed configuration and to permit movement of the biopsy site marker through the side aperture when the flexible deployer is deformed.

14. The marker delivery device of claim 10, the flexible deployer being positioned within the cannula against a side opposite the side aperture when the flexible deployer is in the non-flexed configuration.

15. The marker delivery device of claim 14, the flexible deployer being configured to receive the biopsy site marker between an upper surface of the flexible deployer and the side aperture when the flexible deployer is in the non-flexed configuration.

16. A method of deploying a marker, comprising:
(a) positioning a cannula of a maker delivery device proximate a biopsy site;
(b) translating a rod of the marker delivery device within the cannula of the marker delivery device, the cannula including a closed distal end and a side aperture positioned proximate to the closed distal end;
(c) further translating the rod of the marker delivery device towards the closed distal end to flex a flexible deployer operatively coupled to the rod and positioned proximate to the side aperture, the translating of the rod buckling the flexible deployer to flex a pair of flexible flaps oriented proximate the side aperture via the marker to thereby expel the marker out of the side aperture; and
(d) returning the pair of flexible flaps to an initial position to cover the side aperture and prevent the marker from reentering the cannula.

17. The method of claim 16, further comprising retracting the rod after expelling the marker out of the side aperture under a resilient bias provided by a spring operatively associated with the rod.

* * * * *